United States Patent [19]

Caruso et al.

[11] Patent Number: 5,430,199
[45] Date of Patent: Jul. 4, 1995

[54] METHOD FOR RECOVERING PHENOL AND XANTHENE VALUES FROM BISPHENOL A TARS

[75] Inventors: Andrew J. Caruso; Julia L. Lee, both of Schenectady, N.Y.

[73] Assignee: General Electric Company, Schenectady, N.Y.

[21] Appl. No.: 218,397

[22] Filed: Mar. 28, 1994

[51] Int. Cl.⁶ .............................................. C07C 37/74
[52] U.S. Cl. ................................... 568/724; 568/722
[58] Field of Search .............................. 568/722, 724

[56] References Cited

U.S. PATENT DOCUMENTS

| | | | |
|---|---|---|---|
| 4,131,749 | 12/1978 | Kiedik et al. | 568/781 |
| 4,180,683 | 12/1979 | Mitchell | 568/724 |
| 4,277,628 | 7/1981 | Carnahan | 568/749 |

FOREIGN PATENT DOCUMENTS 1281431 3/1970 Netherlands .

OTHER PUBLICATIONS

Article–By-product of the Bisphenol A reaction. Syntheses and Structure Assignments of 2,4'-Isopropylidenediphenol and 4,4'-(4-Hydrosy-m-phenylenediisopropylidene)-diphenol, FW Neumann and W. E. Smith–J. Org. Chem. Notes, vol. 31 (1966) pp. 4318–4320.
R. J. Michaels–J. Org. Chem. vol. 39, No. 6 (1974)–3 pages.
Article–Solvelysis of Xanthenyl & Fluoronyl Ion Pair 1,2-Dimethylxanthene, H. E. Zougg and J. S. Nowick et al. American Chem. Society (1990) pp. 8902–8906.
Article–Convergent Functional Groups. 9. Complexation in New Molecular Clefts, J. S. Nowick et al. American Chem. Society (1990) pp. 8902–8906.
Article–Analogues des Tetrahydrocannabinols et produits apparentes–II–Syntheses dans la serie du xanthene, Jean-Bernard Chazan and Guy Ourisson (In French) Bulletin De La Societe Chimique De France (1968) No. 4–pp. 1384–1393.
Article–Analogues des Tetrahydrocannabinols et produits apparentes. I–Produits de Condensation de la pulegone et de l'orcinol en presence de POCl3, Jean-Bernard Chazan and Guy Ourisson (In French) Bulletin De La Societe Chimique De France (1968) No. 4–pp. 1374–1384.
Article–Exhaustive C-Methylation of Ketones by Trimethylaluminum, A. Meisters and T. Mole, Aust. J. Chem. (1974) 27, pp. 1655–1663.

*Primary Examiner*—Werren B. Lone
*Attorney, Agent, or Firm*—William H. Pittman

[57] ABSTRACT

A method is provided for recovering phenol values from bisphenol A tar by treating the bisphenol A tar with an alkyl phenol, such as cresol in the presence of an acid catalyst. In addition to recovering phenol, there is obtained a variety of dialkyl 9,9-dimethylxanthenes which can be converted to dicarboxylic acids and their corresponding diesters which are useful polymer intermediates.

4 Claims, No Drawings

METHOD FOR RECOVERING PHENOL AND XANTHENE VALUES FROM BISPHENOL A TARS

CROSS REFERENCE TO RELATED APPLICATIONS

Reference is made to copending application Ser. No. 08/354,356 filed Dec. 15, 1994 filed concurrently herewith.

BACKGROUND OF THE INVENTION

The present invention relates to a method for treating bisphenol A tar at an elevated temperature with an alkylated phenol, such as cresol, in the presence of an acid catalyst to form phenol and a polyalkylated xanthene. The polyalkylated xanthene can be recovered and used as a heat transfer fluid, or in particular instances, can be readily converted to a polyester intermediate, such as a xanthene dicarboxylic acid, dicarboxylic acid halide, or ester thereof.

As shown by Carnahan, U.S. Pat. No. 4,277,628, a bisphenol A waste stream, resulting from the reaction of phenol and acetone in the presence of an acidic condensing agent, can be treated with aluminum isopropoxide to obtain good yields of phenol. Additional methods for recovering phenol and bisphenol A values from bisphenol A waste streams are shown by Kiedik et al, U.S. Pat. No. 4,131,749 and Mitchell, U.S. Pat. No. 4,180,683. Although a number of procedures are available for salvaging bisphenol values from bisphenol A waste streams, or bisphenol A tar, additional methods are constantly being evaluated. The expression "bisphenol A tar" or "bisphenol A waste stream" as used hereinafter, means semi-volatile, or non-volatile organic waste, produced as a by-product in the manufacture of bisphenol A consisting essentially of the following organic compounds:

bisphenol A (5-95% by weight)
o,p-bisphenol A (0-95% by weight)
bisphenol-indan (0-50% by weight)
4-(4-hydroxyphenyl)-2,2,4-trimethylchroman (0-50% by weight)
2-(4-hydroxyphenyl)-2, 4,4-trimethylchroman (0-50% by weight)
trisphenol A (0-95% by weight);
other products containing acetone and phenol residues arising from acid treatment of phenol and acetone (0-80%).

SUMMARY OF THE INVENTION

The present invention is based on the discovery that a bisphenol A tar can be transformed with an alkylphenol, such as m or p cresol, or a mixture thereof, or a dialkylphenol, such as 3,4-dimethylphenol, in the presence of an acid catalyst. There is produced a nearly quantitative yield of phenol and a satisfactory yield of a polyalkylated 9,9-dimethylxanthene substituted with from 2-4 $C_{(1-4)}$alkyl radicals, where the polyalkylated xanthene is included within the formula,

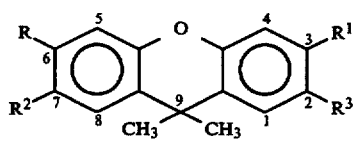

where R, $R^1$, $R^2$, and $R^3$ are members selected from the group consisting of the same or different $C_{(1-4)}$alkyl radicals, and a mixture consisting of hydrogen and the same or different $C_{(1-4)}$alkyl radicals.

It also has been found further that certain of the polyalkylated xanthenes included within formula (1) can be readily oxidized to xanthene dicarboxylic acids. These polyalkylated xanthenes can be substituted with two $C_{(1-4)}$alkyl radicals, which can be the same or different, and located in the 3, 6 position, the 2,7 position, or the 2,6 or 3,7 position. These 9, 9-dimethyl substituted xanthenes can be made using an acid catalyst with an alkyl phenol and a bisphenol A containing material, which hereinafter means a bisphenol A tar, a bisphenol A waste stream, or a material, such as commercial grade bisphenol A, or "off spec" bisphenol A. Such xanthenes can be readily oxidized to xanthene dicarboxylic acids selected from the group consisting of

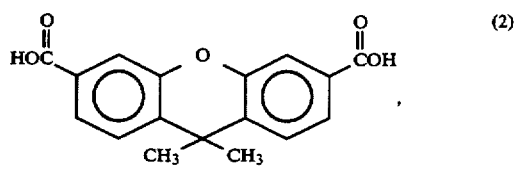

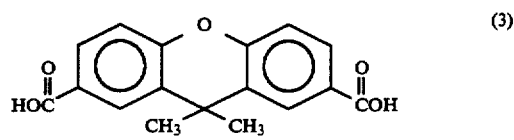

and

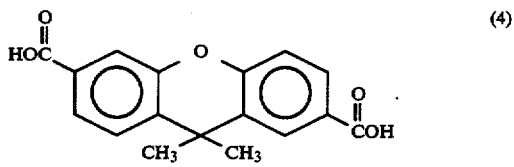

The xanthene dicarboxylic acids of formulas 2–4 also can be converted to their corresponding dialkyl esters, such as the 3,6 dimethyl ester, the 2,7 diethyl ester, or the 2,6 dipropyl ester, by procedures shown hereinafter.

STATEMENT OF THE INVENTION

There is provided by the present invention, a method for recovering phenol values and polyalkylated xanthenes of formula (1) from a bisphenol A tar comprising, (a) forming a mixture at a temperature of from about 90° C. to 200° C. which comprises by weight, from about 1 part to about 50 parts of bisphenol A tar, per 100 parts by weight of a $C_{(1-4)}$alkyl phenol selected from the group consisting of a meta substituted $C_{(1-4)}$alkyl phenol, a para substituted $C_{(1-4)}$alkylphenol, a mixture thereof, and a 3,4-di $C_{(1-4)}$alkyl substituted phenol, in the presence of an effective amount of an acid catalyst, (b) distilling from the resulting mixture of (a), a phenolic material consisting essentially of a member selected from the group consisting of a mixture of phenol and a $C_{(1-4)}$alkyl phenol, a mixture of phenol and a 3,4 di-$C_{(1-4)}$alkyl phenol, a $C_{(1-4)}$alkyl phenol,and a 3,4 di-$C_{(1-4)}$alkyl phenol, and, (c) recovering phenol from the distillate and a polyalkylated xanthene of formula (1) from the residue of (b).

In another aspect of the present invention, there is provided a method for making a xanthene dicarboxylic acid selected from the group consisting of a member shown by formulas (2)–(4), and a mixture thereof, comprising,
- (d) forming a mixture at a temperature of from about 90° C. to about 200° C., which comprises by weight, from about 1 part to about 50 parts of a bisphenol A containing material, per 100 parts by weight of an alkyl substituted phenol selected from the group consisting of a meta substituted $C_{(1-4)}$alkyl phenol, a para substituted $C_{(1-4)}$alkyl phenol, or a mixture thereof, in the presence of an effective amount of an acid catalyst,
- (e) distilling from the resulting mixture of (d), a phenolic material consisting essentially of a member selected from the group consisting of a mixture of phenol and the $C_{(1-4)}$alkyl phenol, and the $C_{(1-4)}$alkyl phenol, and
- (f) recovering a 9,9-dimethylxanthene from the residue of (e), substituted with two $C_{(1-4)}$alkyl radicals which can be the same or different and located in the 3,6 position, the 2,7 position, or a mixture thereof, and
- (g) oxidizing the xanthene of (f) to form a xanthene dicarboxylic acid, or mixture thereof.

There are included within the polyalkylated xanthenes of formula (1), compounds such as 3,6,9,9-tetramethylxanthene, 2,7, 9, 9-tetramethylxanthene, 2, 6, 9, 9-tetramethylxanthene, or mixtures thereof, and 2,3, 6, 7, 9, 9-hexamethylxanthene.

The polyalkylated xanthenes of formula (1) include materials having reasonably low melting points, are high boiling, and have an agreeable odor. They can be used as heat transfer fluids. In addition, as previously described, bisphenol A containing materials can be used to make dialkyl substituted 9, 9-dimethylxanthenes which can be converted to valuable intermediates, such as xanthene dicarboxylic acids within formulas (2)–(4).

Among the xanthene dicarboxylic acids of formulas (2)–(4), there are included:
- 9, 9-dimethylxanthene-3,6-dicarboxylic acid,
- 9, 9-dimethylxanthene-2,7-dicarboxylic acid,
- 9, 9-dimethylxanthene-2,6-dicarboxylic acid or mixtures of these compounds.

The xanthene dicarboxylic acids of formulas (2)–(4), can be converted to their corresponding dialkyl esters by standard esterification procedures using aliphatic alcohols such as, methanol, ethanol, isopropanol and butanol. Among the preferred dialkyl esters, there are included the methyl and ethyl esters.

In addition to monoalkyl phenols, such as m-and p-cresol, some of the dialkyl phenols which can be used in the practice of the invention are 3,4-dimethylphenol, 3-ethyl-4-methylphenol, 4-ethyl-3-methylphenol, 4-butyl-3-methylphenol, and 3-butyl-4-methylphenol.

In the practice of one form of the invention, the bisphenol A tar is treated with the alkyl phenol in the presence of an acid catalyst. Suitable acid catalysts which can be used in the practice of the invention, are for example methanesulfonic acid, toluenesulfonic acid, camphorsulfonic acid, various aromatic mono- and disulfonic acids as well as resin bound catalysts as exemplified by Nafion ® ion exchange beads. An effective amount of acid catalyst is 0.1% by weight to 50% by weight based on the total weight of bisphenol A tar, or bisphenol A containing material.

Experience has shown that distillation of phenolic materials from the polyalkylated xanthene reaction mixture can be effected at a temperature of 70° C. to 240° C. and preferably 70° C. to 90° C. A pressure of from about 0.1 torr to about 760 torr can be used. Separate recovery of phenol, free of alkyl phenol, can be achieved in a subsequent distillation step as shown by Wust et al, U.S. Pat. No. 4,325,789 which is incorporated herein by reference. A component such as chlorotoluene can form an azeotrope with the phenol to effect separation from the cresol. Final recovery of the phenol can be achieved by a second distillation in the presence of water.

The polyalkylated xanthenes can be obtained by distillation which can be effected at a temperature of 120° C. to 280° C. and a pressure of 0.01 torr to 1 torr. Alternatively, the polyalkylated xanthene can be separated from the reaction mixture by a standard recrystallization procedure.

Oxidation of the dialkylated xanthenes can be effected using a pressure reactor at a temperature of 120° C. to 200° C. and a pressure of 250 psi to 450 psi. Suitable oxidizing agents are for example, salts of cobalt and manganese in the presence of HBr, oxygen, and a radical initiator, such as di-t-butyl peroxide in combination with a solvent, such as acetic acid. Alternatively a stoichiometric amount of sodium dichromate in water also can be used. The reactor can be allowed to cool, then vented, and the product filtered and allowed to air dry.

In order that those skilled in the art will be better able to practice the invention, the following examples are given by way of illustration and not by way of limitation. All parts are by weight unless otherwise indicated.

EXAMPLE 1

A mixture of 1.482g (15.4 mmol) of methanesulfonic acid, 10.46g of bisphenol A tar and 155.1g (1.435 mol) of warm m-cresol, was heated at 150°–155° C. for 4.5 hr. The mixture was allowed to cool to room temperature, and 1.96g (23.3 mmol) of solid $NaHCO_3$ was added. An aqueous forerun was followed by the distillation of a mixture of phenol and cresol at atmospheric pressure and at 1 torr. There were obtained 4 fractions containing a total of about 7.4g of phenol and about 133.4g of m-cresol. As shown in U.S. Pat. No. 4,325,789, which is incorporated herein by reference, separation and recovery of the phenol can be readily effected by including in the mixture a component which can form an azeotrope with the phenol, such as chlorotoluene. Separation of the phenol from the chlorotoluene can be achieved by a second distillation in the presence of water.

There was added to the residue of the above reaction mixture, 200 mL of toluene and 200 mL of a 10% NaOH solution. The mixture was stirred overnight at ambient temperature. The organic layer was washed with 3×200 mL of 10% NaOH, 3×200 mL water, and brine, then dried over $MgSO_4$. It was then concentrated under reduced pressure. There was obtained 9.30 g of a brown oil. A Gas Chromatograph interfaced with a Mass Spectrometer (GCMS) showed it was crude 3,6,9,9-tetramethylxanthene at 82% purity. GCMS also showed 3,9,9-trimethylxanthene and 9,9-dimethylxanthene as the principal impurities. A portion of the crude 3,6,9,9-tetramethylxanthene-containing product (8.66 g) was vacuum distilled to give 7.44 g of a fraction boiling at 160°–190° C. (1 torr) which was shown by gas chromatography to consist mainly of 3, 6, 9, 9-tetramethylxanthene. This material was found to have an agreeable odor and it would be useful as a heat transfer fluid.

A 5 g sample of the 3, 6, 9, 9-tetramethylxanthene was charged to a 300 mL pressure reactor equipped for stirring along with 162 mg Co(OAc)$_2$·(H$_2$O)$_4$, 168 mg Mn(OAc)$_2$·(H$_2$O)$_4$, 328 mg di-t-butyl peroxide, 326 mg 48% HBr and 160 mL acetic acid. The reactor was sealed and pressurized to 370 psig with oxygen and the temperature was raised to 130°–160° C. for 5 hrs. After cooling, the reactor was vented and the contents filtered on a fritted disc. The resulting off-white solid was washed with water and air dried. There was obtained, 3.57 g of a cream colored powder. Based on method of preparation, the product was 9, 9-dimethylxanthene-3, 6-dioic acid. Its identity was further characterized by $^1$H-NMR(DMSO-d$_6$) δ13.03 (br s, 2H), 7.68 (s, 4H), 7.56 (s, 2H), 1.61 (s, 6H).

EXAMPLE 2

A mixture of 50.00 g (0. 219 mole) of bisphenol A, 1.0 liter (9.57 mole) of m-cresol, and 19.00 g of methanesulfonic acid, was stirred and heated at 145°–150° C. for 50 hrs. The mixture was allowed to cool and most of the m-cresol was distilled off at about 1 torr. There was added to the mixture, 500 mL of toluene and a saturated aqueous solution of NaHCO$_3$. The organic layer was washed twice with saturated NaHC$_3$ solution and water, dried over MgSO$_4$ and concentrated. An oily residue was distilled twice under vacuum (1 torr). A (150°–178° C.) fraction was recovered as a waxy semisolid. There was obtained 41.35 g (a 72% yield at a 91% purity). Based on the method of preparation, the product was 3, 6, 9, 9-tetramethylxanthene. Its identity was further confirmed by $^1$H-NMR (CDCl$_3$) δ7.25 (d,J=8 Hz, H$_1$), 6.83 (m, H$_2$, H$_4$), 2.28 (s, CH$_3$ benzylic), 1.56 (s, C$_9$—CH$_3$) and $^{13}$C-NMR (CDCl$_3$) 21.0, 32.7, 33.4, 116.7, 123.8, 123.9, 126.0, 127.1, 150.2 ppm.

EXAMPLE 3

There was charged to a pressure reactor, 11.88 g of the tetramethylxanthene of example 2, 127 mg of Co(OAc)$_2$·(H$_2$O)$_4$, 128 mg of Mn(OAc)$_2$·(H$_2$O)$_4$, 248 mg of di-t-butyl peroxide, 125 mL of acetic acid and 248 mg of 48% HBr. The reactor was pressurized with 300 psi of oxygen. The temperature was raised to 170° C. for a period of 4 hrs. The vessel was allowed to cool and then vented. There was obtained 10.456 g of a white solid after filtration and drying having a mp>326. Based on method of preparation, the product was 9, 9-dimethylxanthene-3, 6-dicarboxylic acid.

Example 4

A reaction mixture of 103.10 g (0.438 mol) of bisphenol A, 20.28 g (0.29 mol) of methanesulfonic acid and 2.0 liters of p-cresol was stirred and heated at 140° C. for 66 hrs. After cooling, most of the excess p-cresol was distilled from the reaction mixture at ~1 torr. The pot residue was diluted with toluene (200 mL) and washed with 5% NaOH solution (2×200 mL) and water (2×200 mL). The toluene layer was then concentrated under reduced pressure to afford 147.7 g of a dark, oily solid. It was distilled at 0.5 torr to give a fraction boiling at 138°–140° C. which was shown by gas chromatography and NMR to be 2,7,9, 9-tetramethylxanthene of 91% purity. There was obtained 15.37 g, it had a mp 79°–84° C. It was found to have an agreeable odor and would be useful as a heat transfer fluid. $^1$H-NMR (CDCl3) showed δ7.16 (br s, 2H), 6.92 (m, 4H), 2.30 (s, 6H), 1.59 (s, 6H): $^{13}$C-NMR (CDCl3): 21.1, 32.6, 34.0, 116.2, 126.6, 128.1, 129.8, 132.1, 148.5 ppm.

A mixture of 14.36 g, of 2,7,9, 9-tetramethylxanthene, 162 mg of Co(OAc)$_2$·(H$_2$O)$_4$, 168 mg of Mn(OAc)$_2$·(H2O)$_4$, 328 mg of di-t-butyl peroxide, 326 mg of 48% HBr and 160 mL acetic acid was charged to a 300 mL pressure reactor and pressurized to 300 psi with oxygen. The reaction vessel was then heated to 130°–160° C. for 4.5 hrs. The vessel was allowed to cool and was then vented. The product mixture was filtered on a fritted funnel and washed with water to give, after air drying, 15.22 g, of 9, 9-dimethylxanthene-2,7-dicarboxylic acid as a white solid.

There was charged to a 500 mL round bottomed flask equipped with a reflux condenser, nitrogen inlet and magnetic stirrer, 10.00 g, (33.6 mmol) of 9, 9-dimethylxanthene-2,7-dicarboxylic acid, 250 mL of methanol and 3.0 mL of concentrated sulfuric acid. The mixture was heated to reflux for 16 hours and allowed to cool affording a copious precipitate. A solid was obtained which was filtered on a fritted disc, washed with water and air dried. There was obtained 5.72 g of an off-white crystalline solid, mp 150°–151° C. Based on method of preparation, the solid was dimethyl 9,9-dimethylxanthene-2,7-dioate. $^1$H-NMR (CDCl$_3$) δ88.15 (d, J=2 Hz, 2H), 7.91 (d, d, J=2,8 Hz, 2H), 7.09 (d, J=8 Hz, 2H), 3.92 (s, 6H), 1.69 (s, 6H). $^{13}$C-NMR (CDCl$_3$) 32.8, 34.1, 52.1, 116.6, 125.5, 128.7, 129.3, 148.7, 153.2, 166.5 ppm. Analysis for C$_{19}$H$_{18}$O$_5$; Calc: 326.1154; Found: 326.1180. The filtrates afforded 2.87 g of additional diester.

EXAMPLE 5

A mixture of 27.36 g bisphenol A, 150 mL m-cresol and 150 mL p-cresol was warmed to 80° C. To this solution was added 2.0 mL methanesulfonic acid and the mixture was heated at 125°–135° C. for 45 hours. GCMS of the reaction mixture at this point indicated a relative amount of about 13% of 2,7,9,9-tetramethylxanthene, about 62% of 2, 6, 9, 9-tetramethylxanthene, and about 25% of 3, 6, 9, 9-tetramethylxanthene, based on the total tetramethylxanthene content. The reactor was fitted with a distillation head and excess m- and p-cresol containing phenol was distilled from the reaction mixture at 1 torr. Two fractions boiled at 75° C. (199.38 g) and 85° C. (83.53 g). These were shown by gas chromatography to contain 9.7 and 1.2 percent by weight of phenol respectively. As shown in U.S. Pat. No. 4,325,789, which is incorporated herein by reference, separation and recovery of phenol from mixtures with cresols can be readily achieved by including in the mixture, a component which can form an azeotrope with the phenol, such as chlorotoluene.

There was added to the residue of the above reaction mixture, 100 mL of toluene and 100 mL of a 10% NaOH solution. The mixture was stirred overnight and the organic layer was washed with 200 mL 10% NaOH (2×), 200 mL water (3×) and 200 mL brine. After drying over MgSO$_4$, the toluene was removed under reduced pressure to afford 21.89 g of a dark oil. A portion of this material (19.89 g) was distilled at 1 torr to give 17.74 g of a fraction boiling at 160°–175° C. which was shown by GCMS to consist of a 1:5:2 mixture of 2,7, 9, 9-tetramethylxanthene; 2,6, 9, 9-tetramethylxanthene and 3, 6, 9, 9-tetramethylxanthene, respectively, containing 2, 9, 9-trimethylxanthene and 3, 9, 9-trimethylxanthene as minor impurities. A portion of this product mixture (14.50 g) was oxidized according to the procedure utilized in Example 1 to afford after filtration and air drying, 12.28 g of a cream colored solid having a mp>300° C. consisting of 9, 9-dimethylxanthene-2,7- dicarboxylic acid; 9, 9-dimethylxanthene-2, 6-dicarboxylic acid and 9, 9-dimethylxanthene-3, 6-dicarboxylic acid. The identity of the mixture further was characterized by $^1$H-NMR (DMSO-d$_6$) δ12.95 (br s, 2H), [8.11 (br s), 7.83 (br d, J~8 Hz), 7.70 (br s), 7.68 (s), 7.57 (br s), 7.18 (d, J=8.3 Hz), 7.17 (d, J=8.5 Hz) all signals gave a total of 6H], 1.62 (s, 6H).

To a 250 mL flask was charged 4.137 g of above mixture of 9, 9-dimethylxanthene-2,7-dicarboxylic acid; 9, 9-dimethylxanthene-2, 6-dicarboxylic acid and 9,9-dimethylxanthene-3,6-dicarboxylic acid, 80 mL of methanol, and 2 mL of concentrated sulfuric acid. The mixture was heated for 24 hrs. at reflux and was then allowed to cool and was concentrated under reduced pressure. The residue was diluted with 100 mL of ethylacetate and washed twice with saturated sodium bicarbonate solution and water. The organic layer was concentrated to afford 4.05 g of a 1:4.1:1.2 mixture of dimethyl 9, 9-dimethylxanthene-2,7-dicarboxylate; dimethyl 9, 9-dimethylxanthene-2, 6-dicarboxylate and dimethyl 9,9-dimethylxanthene-3,6-dicarboxylate as a cream colored solid which was characterized by gas chromatography. The crude product was recrystallized twice from methanol to afford pure dimethyl 9,9-dimethylxanthene-2,6-dicarboxylate which was characterized by gas chromatography and $^1$H-NMR(CDCl$_3$) δ8.14 (d,J=2 Hz, 1H), 7.91 (d,d; J=2, 8.5 Hz; 1H), 7.78 (d,d; J=1.8, 8.1 Hz; 1H), 7.74 (br d, J~2 Hz, 1H), 7.49 (d,J=8 Hz, 1H), 7.09 (d,J=8.5 Hz, 1H), 3.93 (s, 3H), 3.92 (s, 3H) 1.68 (s, 6H); mp 145°–147° C.

Although the above examples are directed to only a few of the many variables involved in the practice of the method of the present invention to provide polyalkylated xanthenes and derivatives formed therefrom, it should be understood that the present invention is directed to a much broader variety of polyalkylated xanthenes, dicarboxylic acids and esters thereof, shown in the description preceding these examples.

What is claimed is:

1. A method for recovering phenol values and polyalkylated xanthene values from a bisphenol A tar comprising,
    (a) forming a mixture at a temperature of from about 90° C. to 200° C. which comprises by weight from about 1 part to about 50 parts of bisphenol A tar, per 100 parts by weight of a C$_{(1-4)}$alkyl phenol selected from the group consisting of a meta substituted C$_{(1-4)}$alkyl phenol, a para substituted C$_{(1-4)}$alkylphenol, a mixture thereof, and a 3,4-di C$_{(1-4)}$alkyl substituted phenol, in the presence of 0.1% to 50% by weight based on the total weight of bisphenol A tar, or bisphenol A containing material of an acid catalyst,
    (b) distilling from the resulting mixture of (a), a phenolic material consisting essentially of a member selected from the group consisting of a mixture of phenol and the C$_{(1-4)}$alkyl phenol, a mixture of phenol and a 3,4-di C$_{(1-4)}$alkyl substituted phenol, a C$_{(1-4)}$alkyl phenol, and a 3,4-di C$_{(1-4)}$alkyl substituted phenol and
    (c) recovering phenol from the distillate and a polyalkylated xanthene from the residue of (b).

2. A method in accordance with claim 1, where the polyalkylated xanthene is a 3,6,9,9-tetramethylxanthene.

3. A method in accordance with claim 1, where the polyalkylated xanthene is a 2,7,9,9-tetramethylxanthene.

4. A method in accordance with claim 1, where the polyalkylated xanthene is a 2,6,9,9-tetramethylxanthene.

* * * * *